United States Patent [19]

Felder et al.

[11] 4,297,513
[45] Oct. 27, 1981

[54] PROCESS FOR THE PREPARATION OF BENZOPHENONE THIOETHERS

[75] Inventors: Louis Felder, Basel; Rudolf Kirchmayr, Aesch, both of Switzerland

[73] Assignee: Ciba-Geigy Corporation, Ardsley, N.Y.

[21] Appl. No.: 153,985

[22] Filed: May 28, 1980

Related U.S. Application Data

[63] Continuation of Ser. No. 39,465, May 16, 1979, abandoned.

[51] Int. Cl.³ .................. C07C 148/00; C07C 149/32
[52] U.S. Cl. ........................................ 568/43; 568/42; 560/107; 560/225; 560/255; 560/52; 564/329; 560/85; 560/194; 260/465 D; 260/465 F; 260/465 E; 260/465 G; 546/192; 544/158; 260/326.84; 544/384
[58] Field of Search ........................... 568/41, 42, 43

[56] References Cited

U.S. PATENT DOCUMENTS 3,397,244  8/1968  Louthan
3,542,880  11/1970  Rohr et al.
3,686,313  8/1972  O'Shea
3,949,002  4/1976  Feasey et al.

OTHER PUBLICATIONS

Sendelar et al., Chem. Abst. vol. 83, #27,917e (1975).
Mameda et al., Chem. Abst., vol. 85, #159561k (1976).
Peach, The Chemistry of the Thiol Group, part 2, pp. 735–739 (1974).
Auwers et al., Chem. Ber. vol. 27, pp 1734–1741 (1894).
Schoenberg, Ann, #436, pp. 216–217 (1924).

Primary Examiner—Natalie Trousof
Assistant Examiner—James H. Reamer
Attorney, Agent, or Firm—Luther A. R. Hall

[57] ABSTRACT

Benzophenone thioethers of the general formula I or Ia

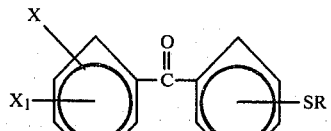

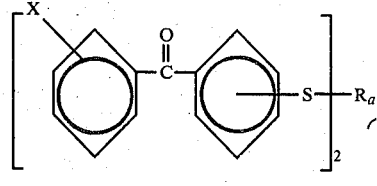

in which X is hydrogen, alkyl, alkoxy or —COO-alkyl and $X_1$ is hydrogen, Cl, Br or —SR, R is an unbranched or branched alkyl radical having 1–20 C atoms, which is unsubstituted or substituted by —OH, —OR$^1$, —O—C(O)—R$^2$, —COOR$^3$, —C(O)-phenyl, —CN, —SR$^1$, —NH$_2$, —NHR$^4$, —NR$^4$R$^5$ or phenyl, in which R$^1$, R$^2$, R$^3$, R$^4$ and R$^5$ are monovalent hydrocarbon radicals, $R_a$ is an alkylene radical having 2–10 C atoms, which is unsubstituted or substituted by —OH, —OR$^1$ or —O—C(O)—R$^2$ and/or is interrupted by —O—, —NR$^4$, —O—C(O)—R$^6$—C(O)—O—, —C(O)—O—R$^7$—O—C(O)— or phenylene and R$^6$ and R$^7$ are divalent hydrocarbon radicals, can be prepared by reacting a mono- or di-halogenobenzophenone of the general formula II

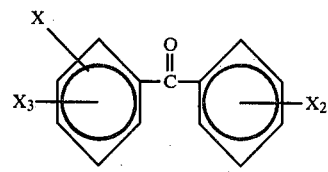

in which $X_2$ is Cl or Br and $X_3$ is H, Cl or Br, in a polar solvent with a mercapto compound of the formula RSH or $R_a$(SH)$_2$ in the presence of a base in an amount equivalent to the amount of halogen to be reacted.

1 Claim, No Drawings

PROCESS FOR THE PREPARATION OF BENZOPHENONE THIOETHERS

This is a continuation of application Ser. No. 039,465, filed on May 16, 1979, now abandoned.

The invention relates to a novel process for the preparation of thioethers of benzophenones from halogenobenzophenones and thiols.

Thioethers of benzophenone have hitherto in the main been prepared by a Friedel-Crafts reaction with aromatic thioethers. For example, K. Auwers and L. Beger in Ber. 27 (1894), 1734 describe the preparation of 4-ethylthio-benzophenone from phenyl ethyl sulfide and benzoyl chloride in the presence of $AlCl_3$. In Ann. 436 (1924), 216, A. Schönberg describes the analogous preparation of 4-methyl-thiobenzophenone. The alkyl aryl sulfides used in these reactions are, however, not readily accessible. Moreover, the Friedel-Crafts reaction falls when alkyl aryl sulfides are used in which the alkyl group is substituted by groups such as hydroxyl or amino groups. However, it is precisely such substituted benzophenone thioethers which recently have achieved importance as photoinitiators for the UV-curing of photopolymerisable systems, for example print pastes, printing plates or paints.

The object of the invention was, therefore, to find a novel process of preparation for benzophenone thioethers which avoids the use of aryl alkyl sulfides and also permits the preparation of benzophenone thioethers which carry, in the aliphatic thioether radical, functional groups which would react with $AlCl_3$ under the conditions of the Friedel-Crafts reaction.

It has now been found that benzophenone thioethers of the general formula I or Ia

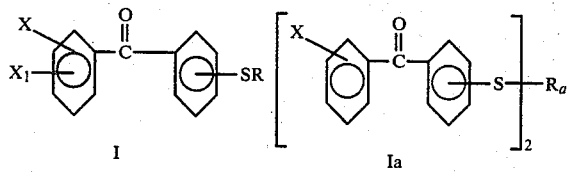

in which X is hydrogen, $C_1-C_4$ alkyl, $C_1-C_4$ alkoxy or —COO—($C_1-C_4$ alkyl) and $X_1$ is hydrogen, Cl, Br or —SR. R is an unbranched or branched alkyl radical having 1–20 C atoms, which is unsubstituted or substituted by —OH, —$OR^1$, —O—$C_4(O)$—$R^2$, —$COOR^3$, —CO-phenyl, —CN, —$SR^1$, —$NH_2$, —$NHR^4$, —$NR^4R^5$ or phenyl, in which $R^1$ is $C_1-C_4$ alkyl, phenyl, $C_7-C_{11}$ alkylphenyl or phenylalkyl; $R^2$ is $C_1-C_{12}$ alkyl, $C_2-C_5$ alkenyl or phenyl; $R^3$ is $C_1-C_{12}$ alkyl and $R^4$ and $R^5$ independently of one another are $C_1-C_8$ alkyl or $C_2-C_4$ hydroxyalkyl, or $R^4$ and $R^5$ together with the N atom to which they are bonded form a pyrrolidine, piperidine, piperazine or morpholine ring, and $R_a$ is an alkylene radical having 2–10 C atoms, which is unsubstituted or substituted by —OH, —$OR^1$ or —O—C-(O)—$R^2$ and/or is interrupted by —O—, —$NR^4$—, —O—C(O)—$R^6$—C(O)—O—, —C(O)—O—$R^7$—O—C(O)— or phenylene, in which $R^6$ is $C_2-C_8$ alkylene, vinylene or phenylene and $R^7$ is $C_2-C_8$ alkylene or 3-oxa-1,5-pentylene, can be prepared by reacting a mono- or di-halogenobenzophenone of the general formula II

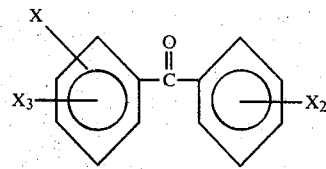

in which $X_2$ is Cl or Br and $X_3$ is H, Cl or Br, in a polar solvent with a mercapto compound of the formula RSH or $R_a(SH)_2$ in the presence of a base in an amount equivalent to the amount of halogen to be reacted.

The amount of base added depends on the number of halogen atoms $X_2$ and $X_3$ to be reacted. If it is desired to react only one halogen atom or if II contains only one halogen atom, one mol equivalent of the base is used per mol of II. If it is desired to react two halogen atoms $X_2$ and $X_3$, two mol equivalents of the base are used. The amount of the mercaptan RSH or $R_a(SH)_2$ used must be at least equivalent to the halogen atoms to be reacted, but it can also be considerably higher.

In the formulae I, Ia and II, the substituents SR, $SR_a$, X, $X_1$, $X_2$ and $X_3$ can be in the ortho-, meta- or paraposition relative to the carbonyl group. The mono- and di-halogenobenzophenones of the formula II are known compounds.

The mercaptans of the formula RSH which are used according to the invention are also known compounds. It is possible to use unsubstituted mercaptans, for example methyl-, ethyl-, isopropyl-, tert.-butyl-, hexyl-, 2-ethylhexyl-, n-octyl-, iso-octyl-, dodecyl-, hexadecyl- or octadecyl-mercaptan. Examples of substituted mercaptans are 2-hydroxyethyl-, 2-hydroxypropyl-, 2-butoxyethyl-, 2-methoxyethyl-, 2-isopropoxyethyl-, 2-phenoxyethyl-, 2-benzyloxyethyl-, 2-(p-tolyloxy)-propyl-, 2-acetoxyethyl-, 3-acetoxypropyl-, 2-propionyloxyethyl-, 2-butyroyloxyethyl-, 2-acryloyloxyethyl-, 3-crotonoyloxypropyl-, 2-benzoyloxyethyl-, 2-methoxycarbonylethyl-, 2-ethoxycarbonylpropyl-, butoxycarbonylmethyl-, iso-octyloxycarbonylmethyl-, 2-benzoylethyl-, 2-cyanoethyl-, 2-methylthioethyl-, 3-aminopropyl-, 2-ethylaminoethyl-, 2-dimethylaminoethyl-, 2-pyrrolidinoethyl-, 2-piperidinoethyl-, 2-morpholinoethyl-, 2-phenylethyl- or benzylmercaptan. The mercaptans used can also be disubstituted, for example 2,3-dihydroxypropyl-, 2-hydroxy-3-butoxypropyl- or 2-hydroxy-3-phenoxypropyl-mercaptan.

Examples of bis-mercaptans of the formula $R_a(SH)_2$ are ethane-1,2-dithiol, butane-1,4-dithiol, hexamethylenedithiol, octamethylenedithiol, 2-hydroxypropane-1,3-dithiol, 2-acetoxypropane-1,3-dithiol, 3-oxa-pentane-1,5-dithiol. di-(2-mercaptoethyl)-butylamine, di-(2-mercaptoethyl)-benzylamine, di-(2-mercaptoethyl) adipate, di-(2-mercaptopropyl) maleate, di-(2-mercaptoethyl) isophthalate, ethylene glycol di-thioglycolate, 2,2-dimethylpropylene di-(2-mercaptopropionate), 1,4-butanediol di-(thioglycolate), diethylene glycol di-(2-mercaptobutyrate), p-xylylenedimercaptan or mi-di-(2-mercaptoethyl)-benzene.

Examples of polar solvents which can be used for the reaction are alcohols, such as methanol, ethanol or isopropanol; glycol ethers, such as butylglycol ether, diethylglycol ether or dimethyldiglycol ether; ketones, such as acetone, methyl ethyl ketone or cyclohexanone; dioxan, dimethylformamide, dimethylacetamide, dimethylsulfoxide, tetramethylenesulfone (sulfolane) or hexamethylphosphoric acid amide. Dimethylformamide or dimethylacetamide are preferably used.

An excess of the mercaptan RSH used can also be used as the solvent since the components and the reaction product are usually readily soluble therein.

Suitable bases are carbonates, hydroxides, oxides, amides, hydrides or alkoxides of alkali metals or alkaline earth metals. Examples are $Na_2CO_3$, $K_2CO_3$, $Li_2CO_3$, $CaCO_3$, NaOH, KOH, MgO, CaO, $LiNH_2$, $NaNH_2$, LiH, NaH, $NaOCH_3$, $NaOC_2H_5$, $KOC_2H_5$ or KO-t-$C_4H_9$.

Strong organic bases, such as quaternary ammonium hydroxides, are also suitable. Alkali metal carbonates or alkali metal hydroxides are preferably used.

Due to the base used, the corresponding base mercaptide forms—at least to some extent—in the reaction mixture. In principle, therefore, it is also possible to use a base mercaptide in place of mercaptan and base. Certain compounds can also be preferentially prepared by the phase transfer process.

It is not necessary for the base used to be soluble in the solvent used; it is merely required that the base mercaptide formed as an intermediate dissolves in the solvent, so that it can react rapidly with the halogenobenzophenone. In order to achieve this solubility and to accelerate the reaction, it is advantageous to carry out the reaction at elevated temperature, preferably at 80° to 140° C. Under these circumstances, the reaction is substantially complete within a few hours.

After the end of the reaction, the base halide formed must be separated from the benzophenone thioether. This can be effected by filtration—if necessary after adding a non-polar solvent—or by washing with water. The resulting crude product can be purified by recrystallisation or distillation. Further details can be taken from the examples given below.

The yields of crude product are about 80-90% and those of pure product are about 70-80%. This is astonishing, since it is known that, in general, it is possible to react aromatically bonded halogen only to a very incomplete extent and only under drastic conditions. Only in those cases where the aromatically bonded halogen has been activated by electron-attracting substituents (halogen or nitro groups) in the ortho- or para-position, for example in the case of 2,4-dinitrochlorobenzene, has it been possible hitherto to prepare aromatic thioethers in this way.

A further surprising advantage of the process is that the reaction of the halogeno-benzophenones with mercaptans which possess a further nucleophilic group, for example a hydroxyl or amino group, proceeds selectively with reaction of the thiol group and formation of the thioethers. The process is particularly suitable for the preparation of compounds of the formula I in which R is an alkyl radical having 1-8 C atoms which is substituted by —OH, —$OR^1$, —O—CO—$R^2$, —$COOR^3$, —CN, —$NH_2$, —$NHR^4$ or —$NR^4R^5$, and $R^1$, $R^2$, $R^3$, $R^4$ and $R^5$ are as defined above.

If the compound used for the reaction is a dihalogenobenzophenone, that is to say a compound of the formula II in which both $X_2$ and $X_3$ are halogen, reaction with at least 2 mol equivalents of RSH and base yields a bis-thioether of the formula I in which X is -SR. On reaction with 1 mol equivalent of RSH and base, on the other hand, monohalogeno-benzophenone monothioethers are obtained.

Preferably, however, monohalogenobenzophenones of the formula II in which $X_3$ is hydrogen are used and reaction with RSH then yields benzophenone monothioethers of the formula I in which $X_1$ is hydrogen. An excess of the mercaptan RSH used has no adverse effects, even when the mercaptan also contains other functional groups. The base, on the other hand, should be used in an equivalent ratio to the number of halogen atoms to be reacted.

Compounds of the formula Ia form from compounds of the formula II in which $X_3$ is hydrogen by reaction with at least 0.5 mol of a dimercaptan of the formula $R_a(SH)_2$ in the presence of 1 mol of base per mol of the compound II.

EXAMPLE 1

4-(2-Hydroxyethyl-mercapto)-benzophenone (a) 17.2 g (0.225 mol) of 2-mercaptoethanol and 15 g (0.225 mol) of KOH (85% pure) in 200 ml of toluene are refluxed under nitrogen in a water separator for 1½ hours. The water separated off is discarded. The toluene is distilled off. 48.8 g (0.225 mol) of 4-chlorobenzophenone and 150 ml of dimethylacetamide are added to the solidified potassium salt. The mixture is stirred for 5 hours at 100° C. The reaction mixture is poured into water and neutralised with acetic acid. The product is taken up in ether. The ether layer is washed with water, dried over $Na_2SO_4$ and concentrated. The resulting product is boiled up with hexane and the crystals are collected. Yield: 44 g (76%). Melting point 49°-52°.

$C_{15}H_{14}O_2S$ calculated: C 69.74, H 5.46, S 12.41%. (258.34) found: C 69.9, H 5.8, S 12.7%.

(b) 11.2 g (0.05 mol) of 4-chlorobenzophenone, 4.3 g (0.055 mol) of 2-mercaptoethanol, 13.8 g (0.1 mol) of calcined $K_2CO_3$ and 15 ml of ethyl methyl ketone are warmed (under reflux) for 16 hours under nitrogen. 50 ml of water are poured over the cooled reaction mixture and the resulting mixture is acidified with HCl. The product is taken up in ether. The ether layer is washed with water, dried over $Na_2SO_4$ and concentrated. The product, which in this case also is obtained as an oil, crystallises on standing. It is boiled up in hexane as described in (a). Yield: 10.0 g (77%). Melting point 49°-51°.

EXAMPLES 2-11

4'-(2-Hydroxyethyl-mercapto)-3,4-dimethyl-benzophenone 12.2 g (0.05 mol) of 4'-chloro-3,4-dimethylbenzophenone and 4.3 g (0.055 mol) of 2-mercaptoethanol in 50 ml of dimethylacetamide are warmed to 95° under nitrogen. 13.8 g (0.1 mol) of calcined $K_2CO_3$ are then added. The suspension is kept at 90°-100° C. for 6 hours. 100 ml of water are poured over the resulting reaction mixture and the product is taken up in ether. The ether layer is washed with water, dried over $Na_2SO_4$ and concentrated. The resulting crystals are recrystallised from methanol and dried in vacuo at 60° C. Yield: 10.1 g (71%). Melting point 92-93° C.

$C_{17}H_{18}O_2S$ calculated: C 71.30, H 6.34, S 11.19%. (286.39) found: C 71.4, H 6.3, S 11.1%.

Further benzophenone derivatives are prepared in the same way. The resulting crude products are recrystallised from a suitable solvent and in some cases also purified through a silica gel dry column (solvent system: chloroform/ethanol, 95:5).

4'-(2-Hydroxyethyl-mercapto)-2,4-dimethyl-benzophenone $C_{17}H_{18}O_2S$ calculated: (71.30, H6.34, S 11.19%. (289.39) found: C71.4, H6.2, S 11.1%, Melting point 64–66° C (ligroin).

4'-(2-Hydroxyethyl-mercapto)-2,5-dimethyl-benzophenone $C_{17}H_{18}O_2S$ calculated: C 71.30, H 6.34, S 11.19%. (286.39) found: C71.1, H 6.4, S 10.5%.

Oil. 4-(2-Hydroxyethyl-mercapto)4'-methyl-benzophenone $C_{16}H_{16}O_2S$ calculated: C70.56, H 5.92, S 11.77%. (272.36) found: C 70.7, H 6.0, S 11.6%.

Melting point 99° C (acetonitrile).

4-(2-Hydroxyethyl-mercapto)-4'-methoxy-benzophenone $C_{16}H_{16}O_3S$ calculated: C 66.65, H 5.59, S 11.12% (288.36) found: C 66.2, H 5.6, S 11.0%.

Melting point 102° C. (ethanol).

4-(2-Hydroxyethyl-mercapto)-4'-isopropyl-benzophenone $C_{18}H_{20}O_2S$ calculated: C 71.97, H 6.71, S 10.67%. (300.42) found: C 71.7, H 6.7, S 10.5%.

Melting point 56° C.

4-(2-Hydroxyethyl-mercapto)-phenyl-thien-2-yl-methanone $C_{13}H_{12}S_2O_2$ calculated: C 59.06, H 4.58, S 24.26% (264.36) found: C 58.6, H 4.5, S 24.3%.

Melting point 65° C. (dry column).

4-(2-Hydroxyethyl-mercapto)-4'-phenoxy-benzophenone $C_{21}H_{18}O_3S$ calculated: C 71.98, H 5.18, S 9.15%. (350.43) found: C 71.6, H 5.1, S 9.1%.

Melting point 122–124° C. (dry column/toluene).

2-(2-Hydroxyethyl-mercapto)-4'-methyl-benzophenone $C_{16}H_{16}O_2S$ calculated: C 70.56, H 5.92, S 11.77, or 11.75%. (272.36) found: C 69.5, H 6.2, S 12.8, or 11.7%. Oil.

2-(2-Hydroxyethyl-mercapto)-benzophenone $c_{15}H_{14}O_2S$ calculated: C 69.74, H 5.46, S 12.41%. (258.34) found: C 68.9, H 5.5, S 13.5%.

Oil.

EXAMPLE 12

4-(2,3-Dihydroxypropyl-mercapto)-benzophenone 14.0 g (0.07 mol) of 4-chlorobenzophenone, 10.0 g (0.93 mol) of 1-thioglycerol and 28.5 g (0.21 mol) of potassium carbonate in 60 ml of dimethylacetamide are kept at 110° C. for 6 hours, under $N_2$ gas and with stirring. After cooling, the reaction mixture is poured into 200 ml of water. The crude product, which is obtained in the form of an oil, is taken up in ethyl acetate, the solution is washed with water until neutral, dried over $K_2CO_3$ and concentrated, isopropanol is poured over the concentrate and the resulting mixture is stirred. The product, which is obtained in the form of crystals, is filtered off. 9.4 g (47%); melting point 86°–88° C.

EXAMPLE 13

4-(2-Dimethylaminoethyl-mercapto)-benzophenone 12.85 g (0.064 mol) of 4-chlorobenzophenone, 13.6 g (0.13 mol) of 2-dimethylaminoethanethiol and 27.6 g (0.2 mol) of potassium carbonate in 100 ml of dimethylacetamide are kept at 100° C. for 12 hours, under $N_2$ gas and with stirring. After cooling, the reaction mixture is poured into 200 ml of water. The oil which separates out is taken up in ether. The crude product is purified by means of hydrochloric acid extract and a bulb tube distillation (bath 200°–220° C./0.01 mm Hg). 10.2 g (59%) of product in the form of an oil are obtained.

EXAMPLE 14

4-Butylthiobenzophenone 27.6 g of $K_2CO_3$ are added to a solution of 21.6 g of 4-chlorobenzophenone and 9.9 g of butylmercaptan in 100 ml of dimethylacetamide and the mixture is stirred at 120°–130° C. for 12 hours under nitrogen. After cooling, the reaction mixture is diluted with 500 ml of water and then extracted with ether. The ether phase is washed with dilute NaOH solution and then with water, dried and evaporated to dryness. The oil residue is distilled in a bulb tube under a high vacuum. After first runnings of a little 4-chlorobenzophenone, 4-butylthiobenzophenone distils in the form of a slightly yellowish coloured oil.

Analysis ($C_{17}H_{18}OS$) calculated: C 75.52 H 6.71 S 11.86%. found: C 75.74 H 6.58 S 11.92%.

What is claimed is:

1. A process for the preparation of 4-(2-hydroxyethyl-mercapto)-benzophenone by reacting 4-chlorobenzopheone with 2-hydroxyethyl mercaptan in dimethylacetamide or dimethylformamide at 80° to 140° C. in the presence of an alkali metal carbonate or alkali metal hydroxide in an amount equivalent to the amount of 4-chlorobenzophenone.

* * * * *